(12) United States Patent
Neumann

(10) Patent No.: US 6,752,832 B2
(45) Date of Patent: Jun. 22, 2004

(54) VERTEBRAL IMPLANT AND SETTING TOOL THEREFOR

(75) Inventor: Carsten Neumann, Bad Abbach (DE)

(73) Assignee: Ulrich GmbH & Co., KG, Ulm (DE)

( * ) Notice: Subject to any disclaimer, the term of this patent is extended or adjusted under 35 U.S.C. 154(b) by 157 days.

(21) Appl. No.: 10/033,046

(22) Filed: Dec. 26, 2001

(65) Prior Publication Data
US 2002/0082695 A1 Jun. 27, 2002

(30) Foreign Application Priority Data
Dec. 27, 2000 (DE) .......................... 100 65 232

(51) Int. Cl.[7] .................................. A61F 2/44
(52) U.S. Cl. ...................... 623/17.15; 606/61
(58) Field of Search .................. 623/17.11, 17.15, 623/17.16; 606/61, 99, 63; 411/190

(56) References Cited

U.S. PATENT DOCUMENTS

| | | | | |
|---|---|---|---|---|
| 4,657,550 A | | 4/1987 | Daher | 623/17.11 |
| 5,533,863 A | * | 7/1996 | Tornquist et al. | 411/285 |
| 5,571,192 A | | 11/1996 | Schonhoffer | 623/17.11 |
| 5,702,455 A | * | 12/1997 | Saggar | 623/17.15 |
| 6,190,414 B1 | * | 2/2001 | Young et al. | 623/17.15 |

FOREIGN PATENT DOCUMENTS

| | | | |
|---|---|---|---|
| DE | 3023942 | 1/1982 | |
| DE | GM-9101603 | 6/1991 | |
| DE | 4423257 | 1/1996 | |
| DE | 19509317 | 9/1996 | |
| DE | 19622827 | 12/1997 | |
| DE | 19804765 | 8/1999 | |
| EP | 0567424 | 10/1993 | |
| GB | 2343726 A * | 5/2000 | F16B/13/02 |
| WO | WO 9846173 A1 * | 10/1998 | A61F/2/44 |
| WO | WO-00/23013 | 4/2000 | |

* cited by examiner

*Primary Examiner*—Brian E Pellegrino
(74) *Attorney, Agent, or Firm*—Herbert Dubno; Andrew Wilford

(57) ABSTRACT

A spinal implant for engagement between a pair of vertebrae has a pair of parts displaceable relative to each other along an axis and each adapted to engage a respective one of the vertebrae. One of the parts is formed with a screwthread engaging a nut that bears axially on the other of the parts and that is formed with an externally accessible array of gear teeth. This implant is set by a setting tool having a holder fittable with the other part, a rotary member in the holder, and a gear on the rotary member meshable with the teeth of the one part when the holder is fitted to the other part.

14 Claims, 12 Drawing Sheets

VERTEBRAL IMPLANT AND SETTING TOOL THEREFOR

FIELD OF THE INVENTION

The present invention relates to a vertebral implant. More particularly this invention concerns such an implant and a tool for setting it in place and adjusting it.

BACKGROUND OF THE INVENTION

When a vertebra is broken or crushed it is frequently necessary to ablate it. Then, in order to prevent the spinal column from collapsing with damage to the fragile spinal cord running in the vertebral foramen forward of the vertebral body, it is necessary to employ a spacer. This device is braced vertically between the bodies of the adjacent vertebra and holds them apart at the desired spacing.

U.S. Pat. No. 5,571,192 describes such an implant which comprises a tubular center element extending along an axis and a pair of end elements. The center element is formed with upper and lower screwthreads of opposite hand and with a plurality of radially throughgoing apertures. The upper and lower tubular end elements are each formed with a plurality of radially through-going aperture, each have a circular-section inner end threaded onto a respective one of the screwthreads, and each also have an outer end adapted to bear on a respective one of the adjacent vertebrae.

Thus such an implant can be set in an area where the body or bodies or one or more vertebra have been ablated. The length of the implant is then increased by rotating the center element to force out the end elements and bring their outer ends into solid engagement with the confronting vertebral surfaces. The screwthreads offer sufficient mechanical advantage that the system can even be used to distract the vertebrae, as is frequently necessary in the event of a crushing injury to a vertebra. The tubular elements of the implant can be filled with bone cement and/or bone fragments to ensure that the implant becomes anchored in place in living bone. Since the outer elements surround the screwthreads of the inner element, once installed the screwthreads will be largely covered so that their sharp edges do not impair healing.

Such an implant has proven very effective in use. It is, however, fairly difficult to position and expand. Thus the surgical field must normally be fairly wide in order to permit the surgeon to get at the center element with a tool and rotate it. Even if each angular stepping of this center element is only through a relatively small angle, it is still necessary to open up the patient quite a bit. Obviously this is not always possible or advisable.

OBJECTS OF THE INVENTION

It is therefore an object of the present invention to provide an improved vertebral implant.

Another object is the provision of such an improved vertebral implant which overcomes the above-given disadvantages, that is which can be set in place and expanded in a relatively reduced surgical field.

A further object is to provide a tool usable with this implant which expands it axially and which requires that the opening be only big enough to pass the implant.

SUMMARY OF THE INVENTION

A spinal implant for engagement between a pair of vertebrae has according to the invention a pair of parts displaceable relative to each other along an axis and each adapted to engage a respective one of the vertebrae. One of the parts is formed with a screwthread engaging a nut that bears axially on the other of the parts and that is formed with an externally accessible array of gear teeth.

It is possible to rotate this nut by means of a tool that can engage through a relatively narrow opening, so that the operating field need merely be wide enough to allow the implant to pass through.

The parts according to the invention are tubular and coaxial. The one part having the screwthread is inside the other part so their interior can be filled with bone chips and/or cement to knit the implant with the vertebrae it is engaging. In addition interengaging formations on the parts preventing relative rotation about the axis. These formations include a radially open and axially extending groove and a radially projecting pin engaged in the groove.

The other outer part has a rim against which the nut fits and is formed with a radially throughgoing notch opening at the rim and having a frustoconical surface acting as a seat for a bevel gear of the setting tool. It is also formed diametrically across from the notch with a radially open threaded hole. The one inner part is formed in line with the notch and hole of the other outer part with respective axially extending and radially throughgoing slots. When bone grows through these slots, it effectively blocks the two parts from rotating relative to each other and thereby shortening the implant.

The other outer part in accordance with the invention is formed with a pair of outwardly open holder grooves symmetrically flanking a plane extending along the axis and bisecting the notch and threaded hole. Furthermore the flange is formed with an array of throughgoing holes. Such a flange allows bone cement to be applied to the end of the implant without getting on the setting tool, and the holes ensure that the flange will bond solidly to the vertebra it engages. The one inner part is formed with a radially projecting flange and the nut lies between the flange and the rim. Furthermore the nut is formed with an axially extending spacer collar engageable axially with the one inner part. The flange is spaced from the one inner part when the collar engages the one inner part.

Such an implant is used according to the invention with a setting tool having a holder fittable with the other part, a rotary member in the holder, and a gear on the rotary member meshable with the teeth of the one part when the holder is fitted to the other part. This rotary member is a rod having one end provided with the gear and an opposite end provided with a hand wheel. The rod is tubular and coaxially receives a core rod having an inner end screwable into the other part. The tool further has an outer tube coaxially surrounding the shaft and having an outer end carrying the holder. The holder is a fork engageable around the other part. This fork is double and has four tines engageable with the other part.

Such a tool can be solidly locked to the implant, with the double fork gripping the outer part and preventing it from rotating about the axis of the tool and the core rod threaded into the outer part also locking it to the tool, so that the implant can be manipulated without any possibility of the coming off the tool. With the core rod extending diametrally through the inner implant part, any relative rotation of these two parts is impossible. Considerable torque can be applied to the core rod to rotate the bevel gear and extend the implant also without any fear of damage to surrounding tissues, since the surgeon can hold the outer tubular shaft in one hand to prevent any rotation of it while turning the core rod with the other hand to expand the implant. This prevents any damage to tissues during the delicate expansion or distraction step.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
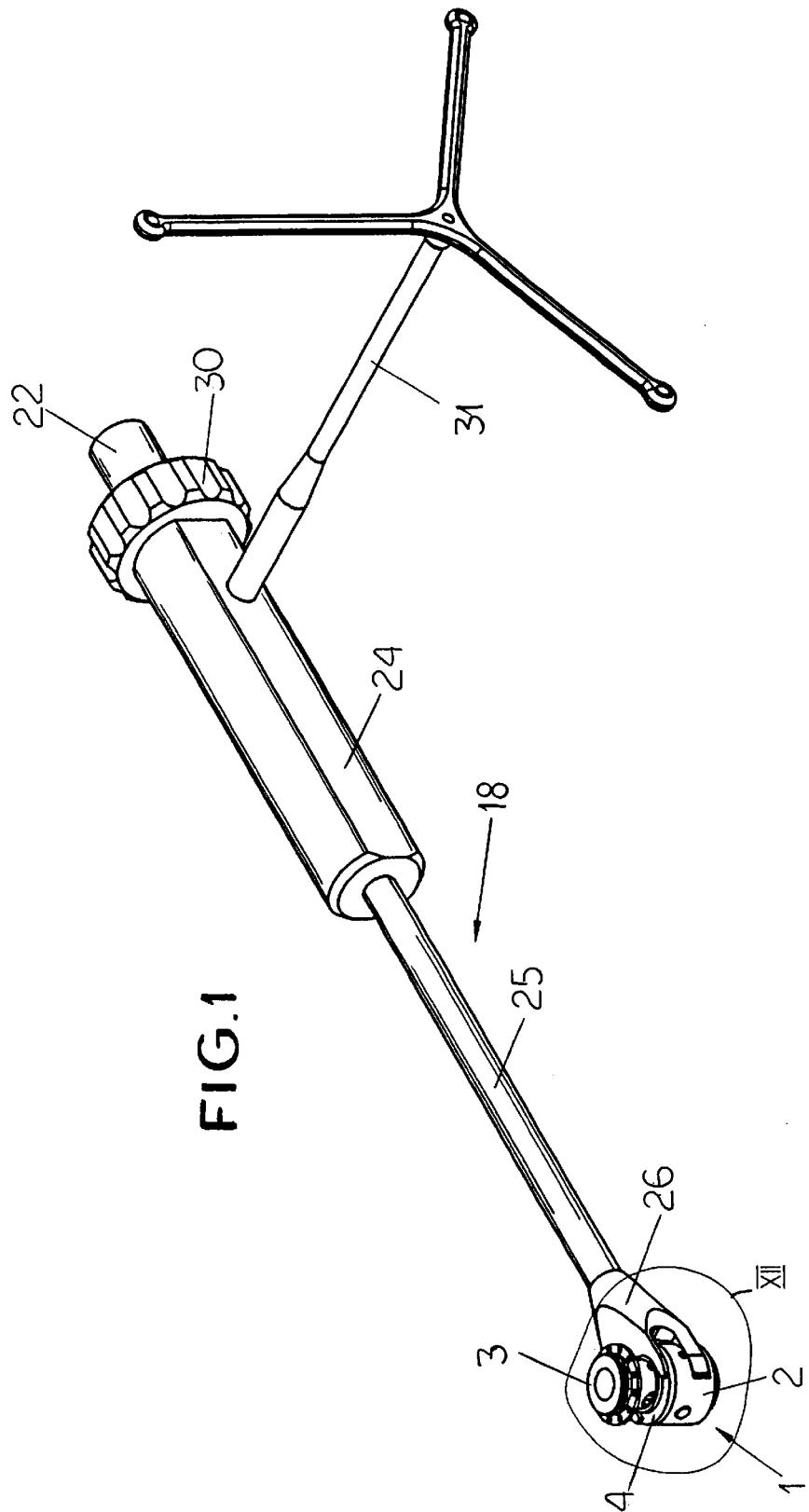
FIG. 1 is a small-scale perspective view of the implant and tool according to the invention.
Figure 2:
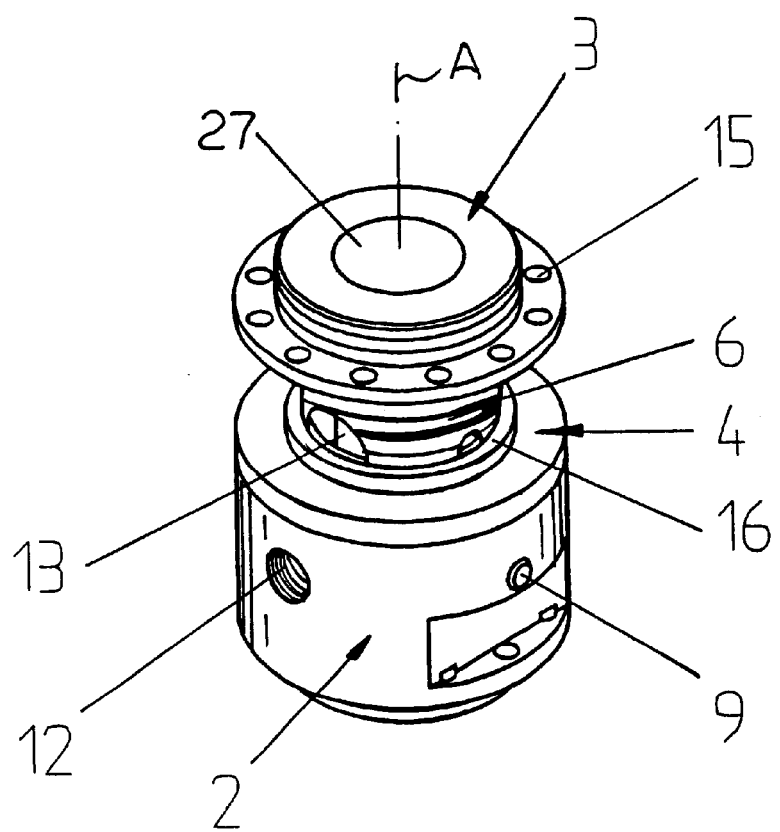
FIG. 2 is a perspective view of the implant in axially extended condition.
Figure 3:
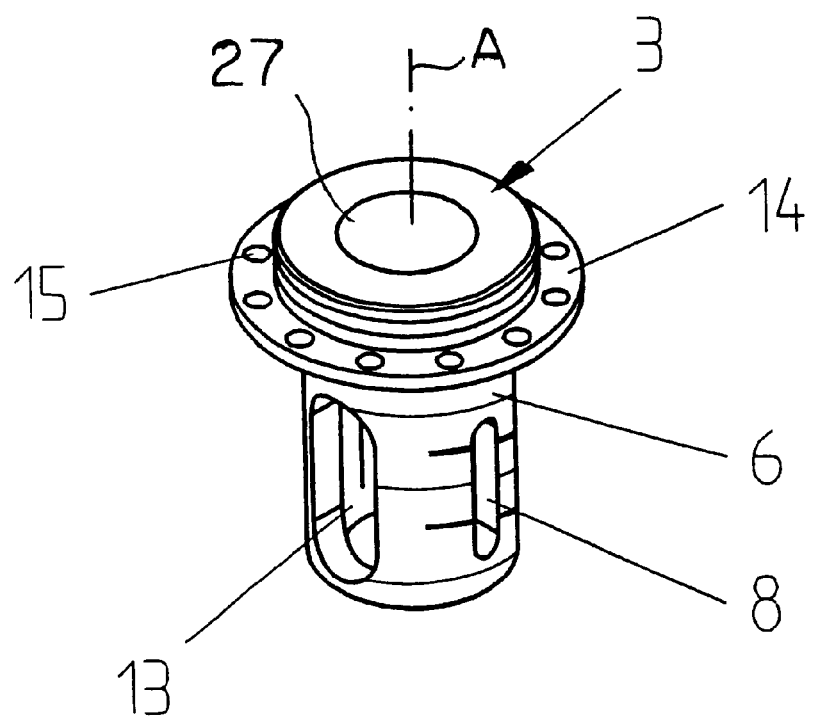
FIGS. 3 and 4 are perspective views of the core and sleeve parts of the implant.
Figure 4:
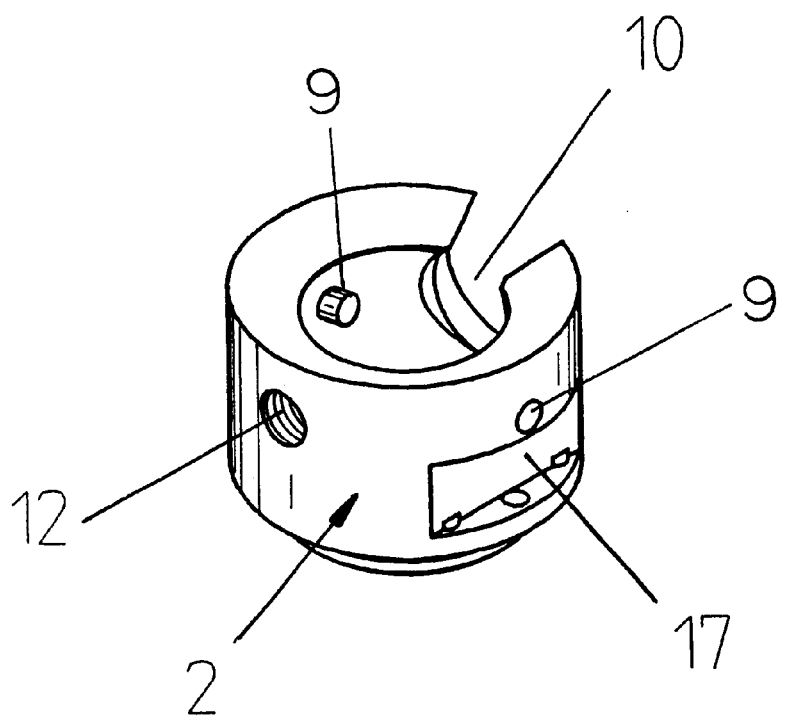
Figure 5:
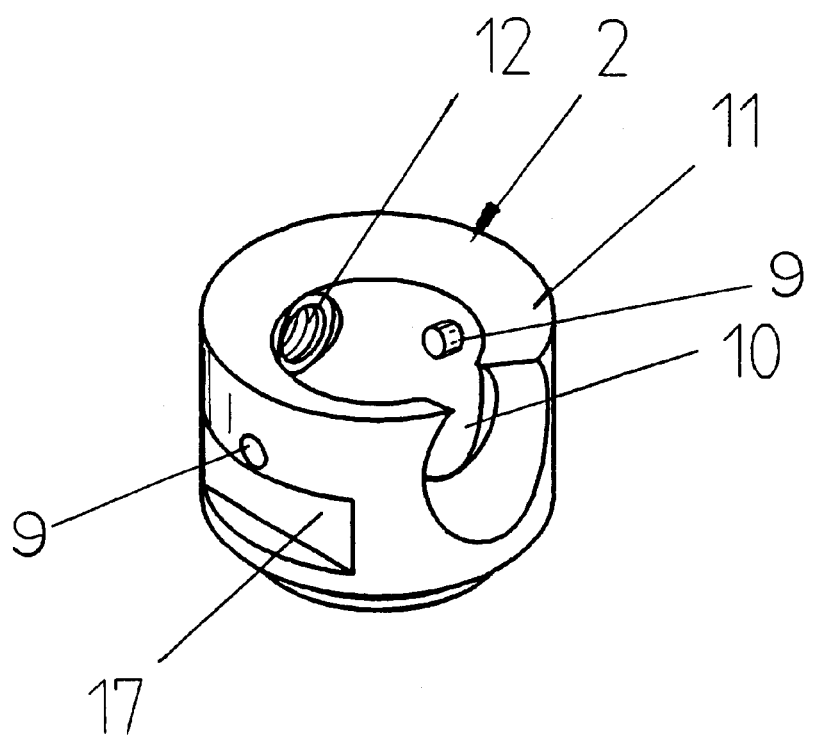
FIG. 5 is another perspective view of the sleeve part taken from a slightly different angle as FIG. 4.
Figure 6:
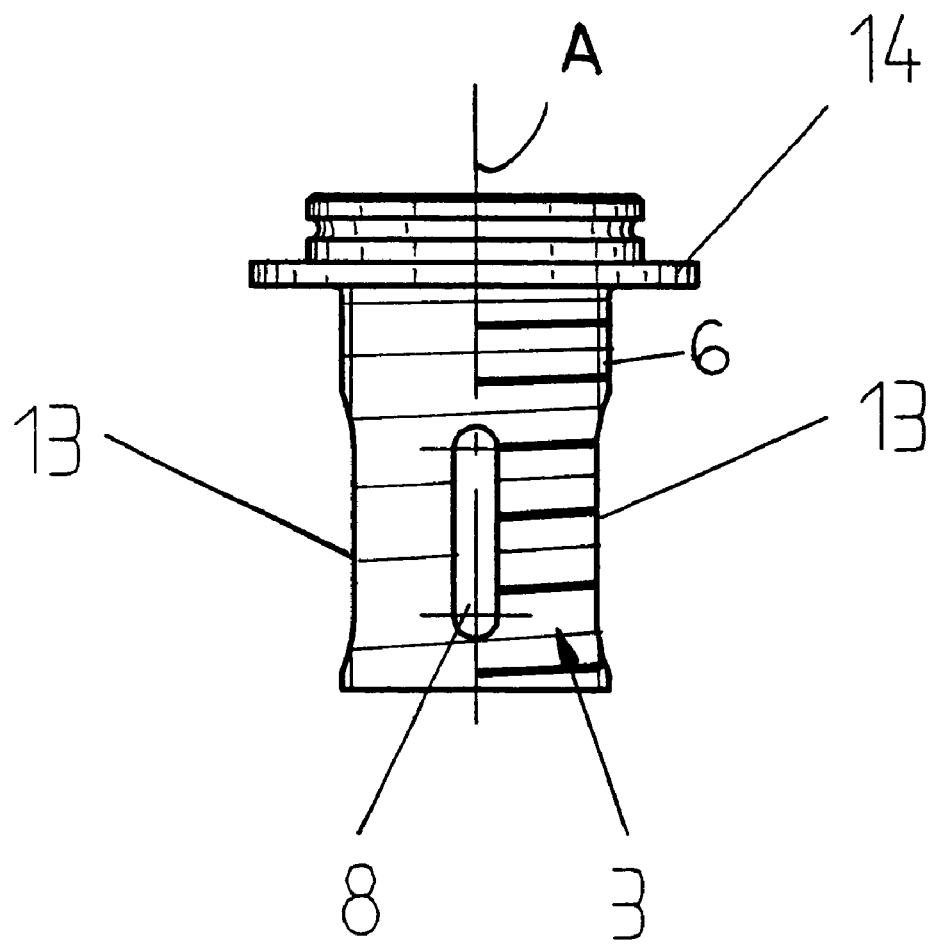
FIGS. 6 and 7 are side views of the core part taken 90° offset from each other.
Figure 7:
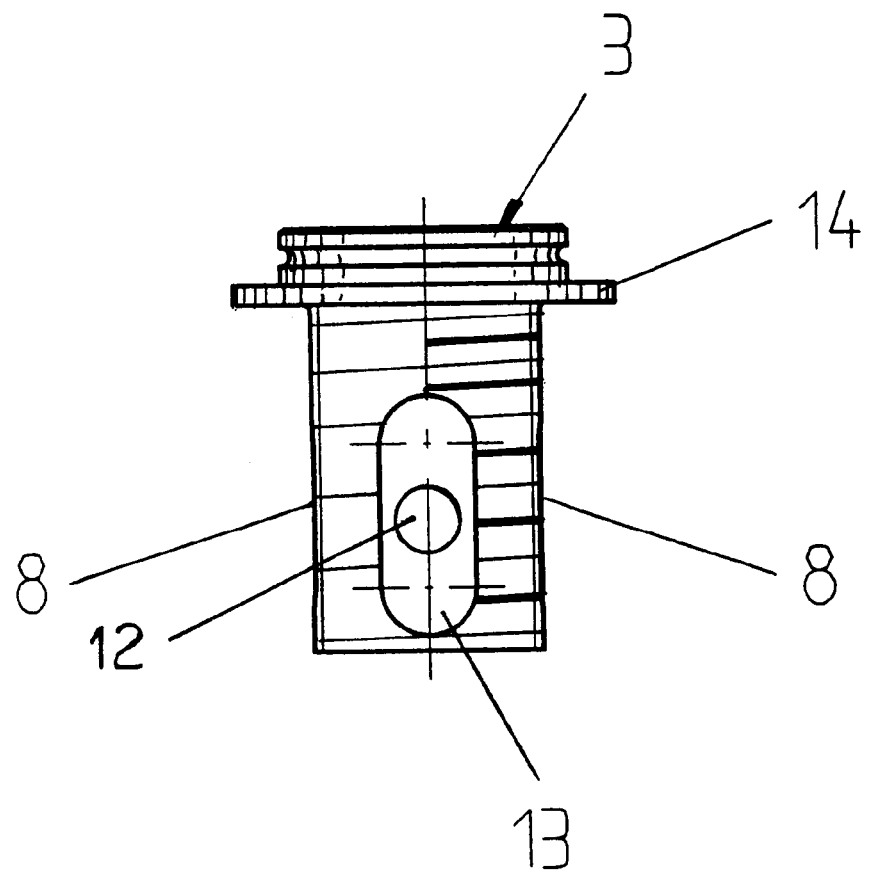
Figure 8:
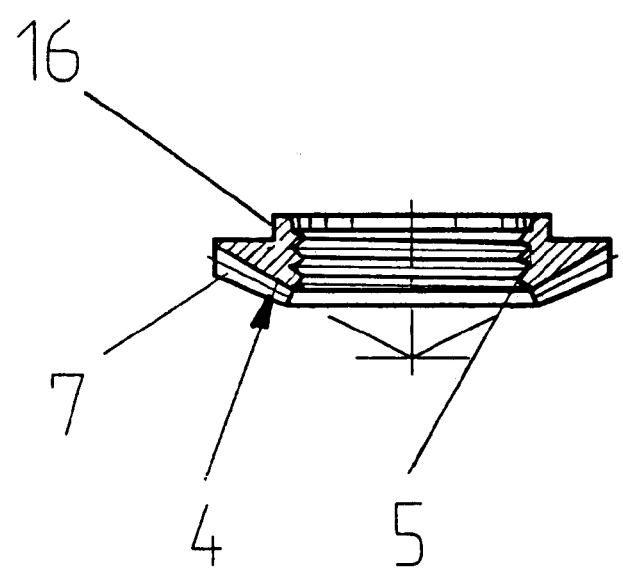
FIG. 8 is an axial section through the nut of the implant.

As seen in FIGS. 1 through 8, a spinal implant 1 basically comprises an outer sleeve part 2, an inner core part 3, and a nut 3, all centered on a common axis A. These parts 2, 3, and 4 are normally all made of a biologically inert metallic alloy.

The nut 4 has an internal helical screwthread 5 (FIG. 8) that engages an external screwthread 6 (FIGS. 2, 3, and 6) of the core part 3 and is formed with an array 7 of bevel-gear teeth 7 imparting to the lower end of the nut 4 a frustoconical shape that fits complementary on an upper rim 11 of the sleeve part 2. In addition the nut 4 has a cylindrical upwardly extending spacer collar 16 centered on the axis A.

The sleeve part 2 is formed with a radially through-going notch 10 (FIGS. 4 and 5) that extends up to the rim 11 and that has an outwardly flared edge. Diametrically opposite this aperture 10 is a small-diameter radially inwardly open threaded hole 12. At its upper end it has a radially outwardly projecting flat flange 14 that can, in a fully shortened or collapsed condition of the implant 1, sit atop the collar 16 of the nut 4 which in turn sits on the surface 11 so as form, even in this condition, a space between the parts 3 and 4. This flange 14 is formed with an array of angularly equispaced and axially throughgoing holes 15.

The core 3 is formed with a pair of diametrically opposite, radially throughgoing, and axially extending narrow slots 8 and, 90° offset therefrom, with a similar pair of wide slots 13. These latter slots 13 are normally aligned with the aperture 10 and hole 12. The sleeve part 2 is further provided with a pair of radially inwardly projecting pins 9 that normally extend into the slots 8 and that rotationally couple the parts 2 and 3 together while allowing them to move axially relative to each other. A pair of outwardly open secantal holder grooves 17 are formed on opposite sides of the sleeve part 2, symmetrically flanking a plane bisecting the notch 10 and hole 12. This core part 3 has an open interior space 27.

Figure 9:
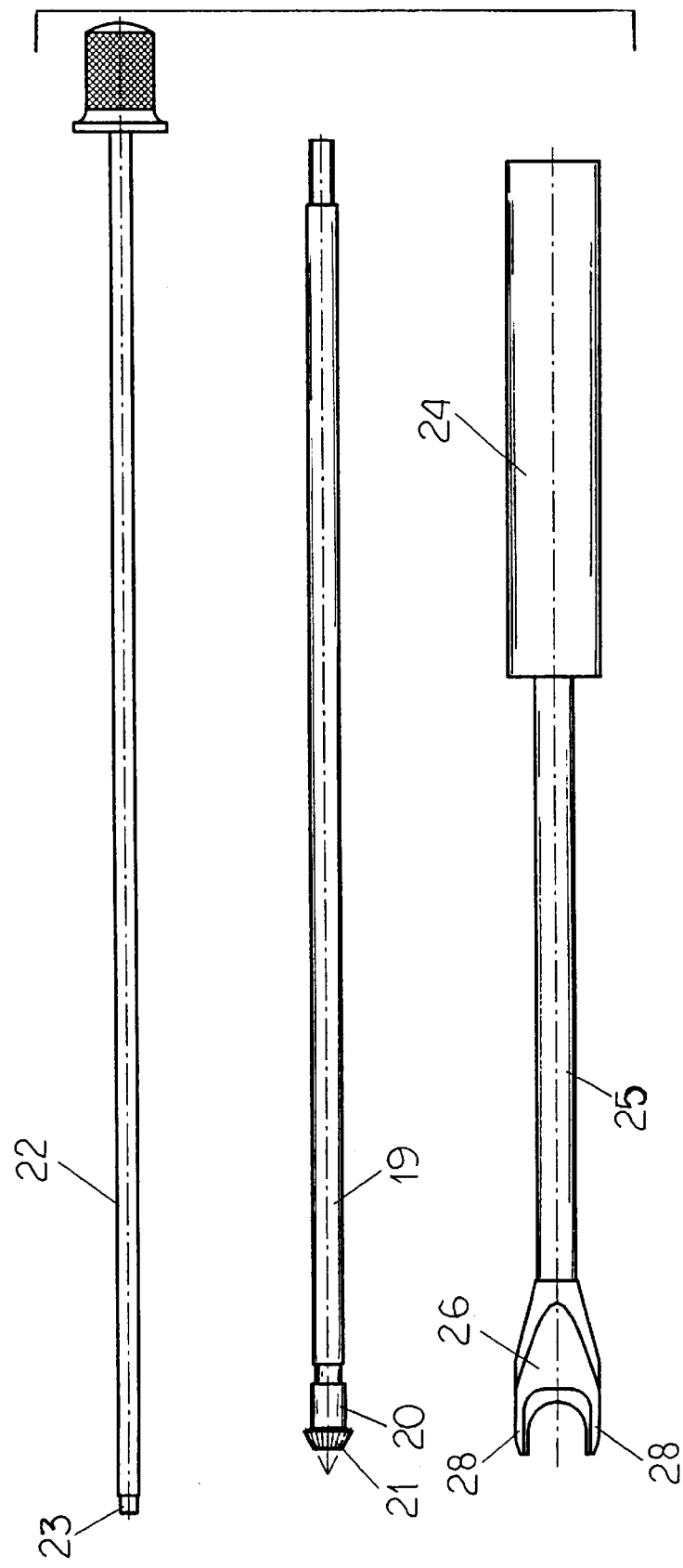
FIG. 9 is a small-scale top view of the parts of the setting tool.
Figure 10:
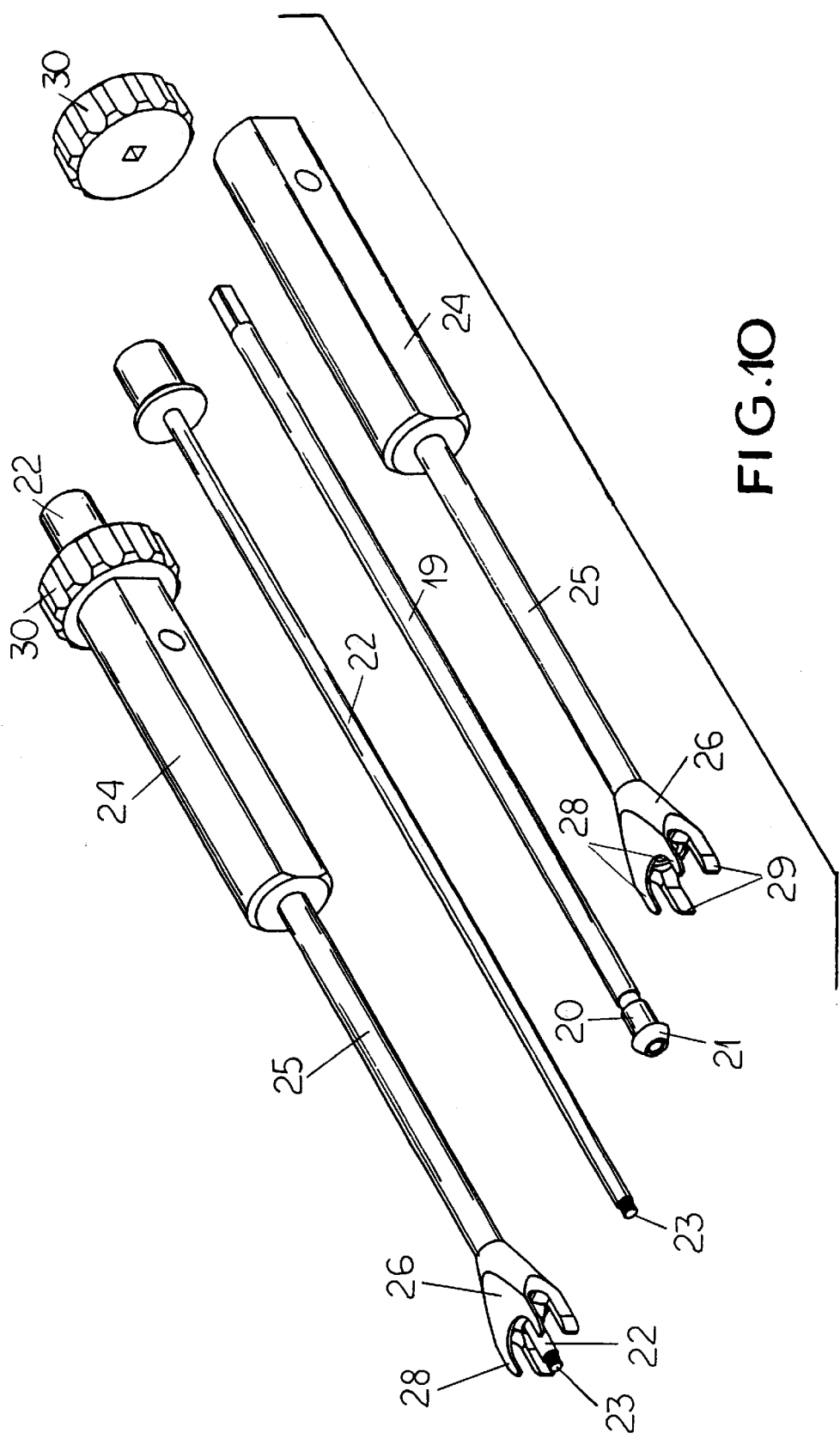
FIG. 10 is a small-scale perspective view of the parts of the setting tool.
Figure 11:
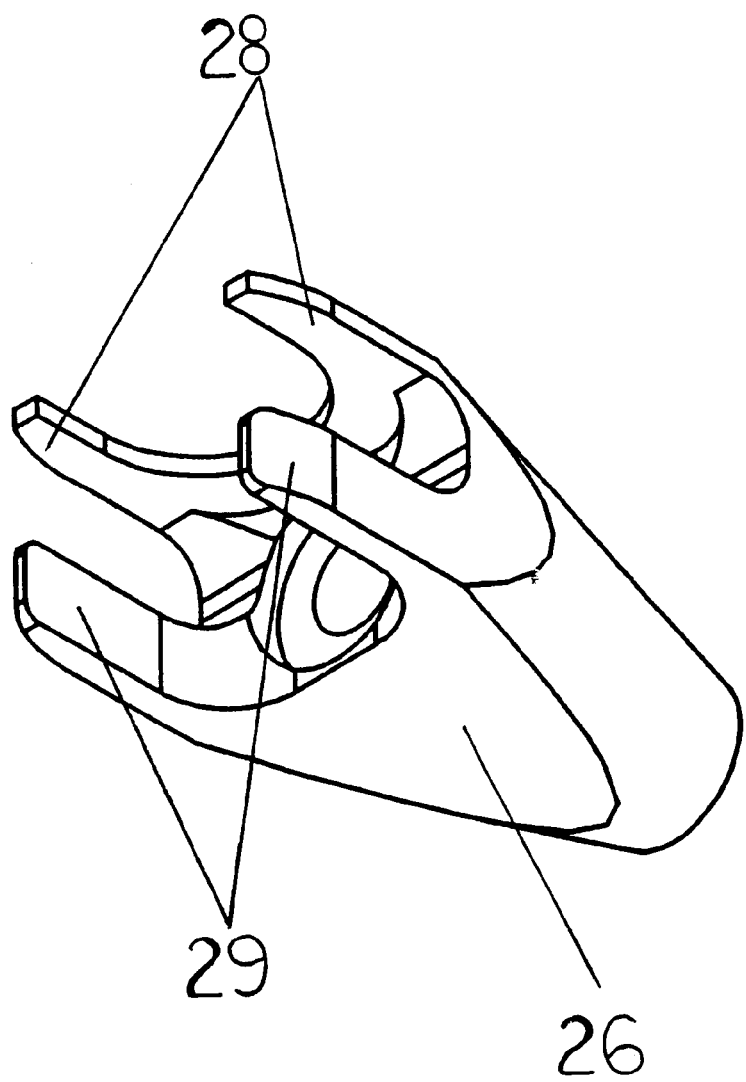
FIG. 11 is a larger-scale view of the holder of the setting tool.
Figure 12:
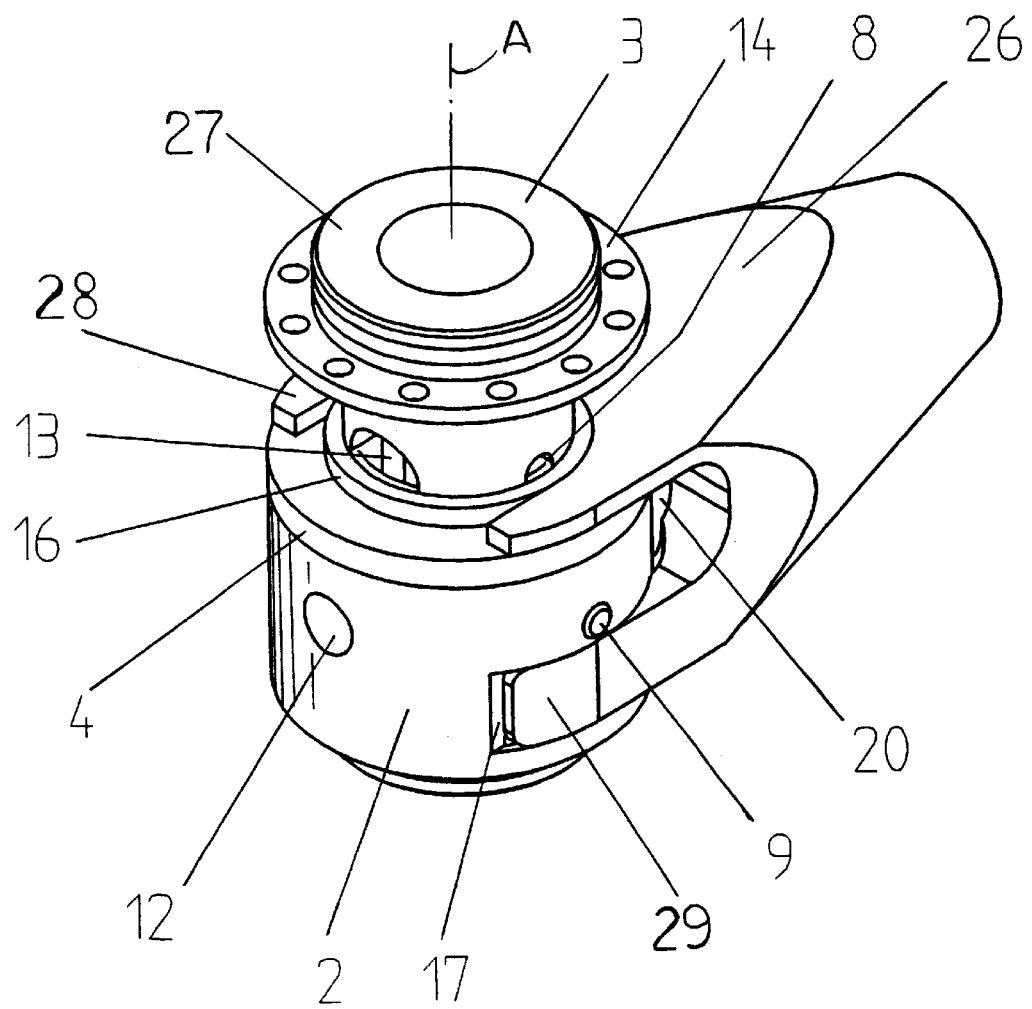
FIG. 12 is a large-scale view of the detail indicated at XII in FIG. 1.

Such an implant is set and expanded by a tool 18 shown in detail in FIGS. 9 through 12. It comprises an inner tube or shaft 19 having at an inner end a bevel gear 20 with teeth 21 engageable with the teeth 7 of the nut 4 and fittable in the aperture 10, and at its opposite end a hand wheel 30. Coaxially inside this shaft 19 is a rod 22 that can pass through the slots 13 and that has a threaded inner end 23 complementarily fittable in the hole 12. Coaxially outside the shaft 22 is an outer tube 25 having an outer-end handle 24 and provided on its inner end with a holder 26 having an upper fork 28 and a lower fork 29. The upper fork 28 is flat and adapted to fit in the narrow groove or space formed between the lower face of the flange 14 and the upper face of the nut 4 and has an axial dimension equal to the length of the collar 16. The lower fork 29 is complementary to the holder grooves 17. A positioning spider 31 that can work with a computer-controlled positioning system is fixed to the side of the handle 24.

To set the implant 1 its parts are fitted together with the nut 4 screwed all the way up on the screwthread 8 of the core part 3 so that the assembly is of minimal axial dimension. It is then fitted to the forks 28 and 29 of the holder 26. This engages the gear 21 on the tubular shaft 19 with the teeth 7 of the nut 4. Then the rod 22 is passed through the slots 13 and its end 23 is screwed into the hole 12. This solidly locks the implant 1 to the inner end of the tool 18.

The insert 1 is then moved into position between the two vertebrae it is to brace and, if necessary distract. The wheel 30 is rotated to turn the shaft 19 and gear 21, thereby rotating the nut 4 so that it screws the core part 3 axially away from the sleeve part 2, axially extending the implant.

Once the implant 1 is solidly in place, the shaft 19 is unscrewed from the hole 12 and the tool 18 is pulled radially of the axis A off the implant 1, leaving the implant 1 in position. This leaves one of the large slots 13 exposed so the interior 27 can be packed with cement and bone chips to ensure that the implant 1 will become integrated into the patient's spine.

I claim:

1. A spinal implant for engagement between a pair of vertebrae, the implant comprising:

a first tubular element having an upper threaded part;

a second tubular element forming an unthreaded part coaxial with and outside the threaded part, the parts being displaceable relative to each other along an axis and each adapted to engage a respective one of the vertebrae; and a nut threadedly engaging the screwthread of the threaded part, bearing axially on the unthreaded part, and formed with an externally accessible array of gear teeth, the unthreaded part having a rim against which the nut fits and being formed with a radially throughgoing notch opening at the rim.

2. The spinal implant defined in claim 1, further comprising interengaging formations on the parts preventing relative rotation about the axis.

3. The spinal implant defined in claim 2 wherein the formations include a radially open and axially extending groove and a radially projecting pin engaged in the groove.

4. The spinal implant defined in claim 1 wherein the unthreaded part is formed diametrically across from the notch with a radially open threaded hole.

5. The spinal implant defined in claim 4 wherein the threaded part is formed in line with the notch and hole of the unthreaded part with respective axially extending and radially throughgoing slots.

6. The spinal implant defined in claim 5 wherein the unthreaded part is formed with a pair of outwardly open holder grooves symmetrically flanking a plane extending along the axis and bisecting the notch and threaded hole.

7. The spinal implant defined in claim 5 wherein the flange is formed with an array of throughgoing holes.

8. The spinal implant defined in claim 1 wherein the threaded part is formed with a radially projecting flange, the nut lying between the flange and the rim.

9. The spinal implant defined in claim 8 wherein the nut is formed with an axially extending spacer collar engageable axially with the threaded part, the flange being spaced from the threaded part when the collar engages the threaded part.

10. In combination:
  a spinal implant for engagement between a pair of vertebrae, the implant comprising
    a first tubular element having an upper threaded part,
    an a second tubular element forming an unthreaded part, the parts being displaceable relative to each other along an axis and each adapted to engage a respective one of the vertebrae, and
    a nut threadedly engaging the screwthread of the threaded part, bearing axially on the unthreaded part, and formed with an externally accessible array of gear teeth; and
  a setting tool comprising
    a holder fittable with the unthreaded part,
    a shaft in the holder having a pair of ends,
    a gear on one of the ends of the shaft meshable with the teeth of the threaded part when the holder is fitted to the unthreaded part,
    a hand wheel on the other end of the shaft, and
    a core rod having an inner end screwable into the unthreaded part.

11. The spinal implant defined in claim 10 wherein the tool further has
  an outer tube coaxially surrounding the shaft and having an outer end carrying the holder.

12. The spinal implant defined in claim 11 wherein the holder is a fork engageable around the unthreaded part.

13. The spinal implant defined in claim 12 wherein the fork is double and has four tines engageable with the unthreaded part.

14. In combination:
  a spinal implant comprising:
    an outer unthreaded tubular sleeve part centered on an axis,
    an inner tubular core part having an upper external screwthread and coaxially received in the outer part,
    means including interengaging formations on the parts for permitting them to move axially relative to each other while preventing them from rotating about the axis relative to each other, and
    a nut threaded on the screwthread of the core part, bearing axially on the sleeve part, and formed with an array of externally accessible gear teeth; and
  a setting tool comprising:
    an elongated body having inner and outer ends,
    a holder on the inner end fittable with the sleeve part,
    a shaft extending through the body and having an inner end projecting at the holder from the body and carrying a gear meshing with the teeth of the nut, and
    a rod extending through the shaft and having an inner end screwable into the sleeve part.

* * * * *